United States Patent
Fujiki et al.

(10) Patent No.: US 11,957,691 B2
(45) Date of Patent: *Apr. 16, 2024

(54) DRUG FOR PREVENTING AND/OR TREATING POLYCYSTIC KIDNEY DISEASE

(71) Applicant: OTSUKA PHARMACEUTICAL CO., LTD., Tokyo (JP)

(72) Inventors: Hiroyuki Fujiki, Osaka (JP); Miki Aihara, Osaka (JP); Shizuo Kinoshita, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/475,451

(22) Filed: Sep. 15, 2021

(65) Prior Publication Data

US 2022/0241293 A1 Aug. 4, 2022

Related U.S. Application Data

(60) Division of application No. 16/225,255, filed on Dec. 19, 2018, now Pat. No. 11,147,821, which is a continuation of application No. 15/473,032, filed on Mar. 29, 2017, now abandoned, which is a division of application No. 14/402,540, filed as application No. PCT/JP2013/065637 on May 30, 2013, now Pat. No. 9,636,382.

(60) Provisional application No. 61/653,524, filed on May 31, 2012.

(51) Int. Cl.
| | |
|---|---|
| *A61K 31/55* | (2006.01) |
| *A61K 9/00* | (2006.01) |
| *A61K 38/10* | (2006.01) |
| *A61K 38/31* | (2006.01) |
| *A61K 45/06* | (2006.01) |

(52) U.S. Cl.
CPC ............ *A61K 31/55* (2013.01); *A61K 9/0019* (2013.01); *A61K 9/0053* (2013.01); *A61K 38/10* (2013.01); *A61K 38/31* (2013.01); *A61K 45/06* (2013.01)

(58) Field of Classification Search
CPC .... A61K 45/06; A61K 9/0019; A61K 9/0053; A61K 31/55; A61K 38/31; A61K 2300/00; A61K 38/10
See application file for complete search history.

(56) References Cited

FOREIGN PATENT DOCUMENTS

| JP | 4-154765 A | 5/1992 |
|---|---|---|
| JP | 2004-505095 A | 2/2004 |
| JP | 2009-521397 A | 6/2009 |
| JP | 2009-526002 A | 7/2009 |
| JP | 2009-539803 A | 11/2009 |
| JP | 2010-531293 A | 9/2010 |
| JP | 6116591 B2 | 4/2017 |
| JP | 6724085 B2 | 7/2020 |
| WO | 91/05549 A1 | 5/1991 |
| WO | 02/10192 A2 | 2/2002 |
| WO | 2005/000893 A2 | 1/2005 |
| WO | 2007/074915 A1 | 7/2007 |
| WO | 2007/096055 A1 | 8/2007 |
| WO | 2007/114697 A1 | 10/2007 |
| WO | 2007/141306 A2 | 12/2007 |
| WO | 2009/001968 A1 | 12/2008 |
| WO | 2013/180310 A1 | 12/2013 |

OTHER PUBLICATIONS

Belibi et al, Novel targets for the treatment of autosomal dominant polycystic kidney disease, Expert Opin. Investig. Drugs, 2010, 19 , pp. 315-328.*
Fonck et al, Autosomal recessive polycystic kidney disease in adulthood, Nephrol Dial Transplant, 2001, 16, pp. 1648-1652.*
Miñano et al, Clinical Pharmacology of Portal Hypertension, Gastroenterol Clin N Am, 2010, 39, pp. 681-695.*
Office Action, dated Oct. 27, 2021, issued by the Vietnamese Patent Office in corresponding Vietnamese Patent Application No. 1-2018-05757.
Miao Hu et al., "Pharmacokinetic evaluation of lanreotide", Expert Opinion on Drug Metabolism & Toxicology, 2010, vol. 6, No. 10, pp. 1301-1312 (12 pages total).
Communication dated Jul. 20, 2020 from the State Intellectual Property Office of the P.R.C. in Application No. 201710751329.5.
Communication dated Feb. 24, 2021 from the Japanese Patent Office in Application 2020-071399.
Communication dated Mar. 18, 2021 from the Intellectual Property Office of the Philippines in Application No. 1-2018-501227.
Annamaria Colao, M.D., Ph.D., et al., "A 12-Month Phase 3 Study of Pasireotide in Cushing's Disease", The New England Journal of Medicine, 2012, vol. 366, No. 10, pp. 914-924 (11 pages total).
PH. Caron et al., "Efficacy of the New Long-Acting Formulation of Lanreotide (Lanreotide Autogel) in the Management of Acromegaly" The Journal of Clinical Endocrinology & Metabolism, 2002, vol. 87 No. 1, pp. 99-104 (6 pages total).
Brett E. Fortune et al., "Vapreotide: a somatostatin analog for the treatment of acute varical bleeding", Drug Evaluation, 2009. vol. 10, pp. 2337-2342 (6 pages total).

(Continued)

*Primary Examiner* — Li N Komatsu

(74) *Attorney, Agent, or Firm* — Sughrue Mion, PLLC

(57) ABSTRACT

An object of the present invention is to provide a combination drug that has remarkably excellent preventive and/or therapeutic effects on polycystic kidney disease. The present invention provides a drug for preventing and/or treating polycystic kidney disease comprising a combination of tolvaptan or a prodrug thereof with a somatostatin derivative, and a method for treating polycystic kidney disease using this drug.

3 Claims, No Drawings

Specification includes a Sequence Listing.

(56) References Cited

OTHER PUBLICATIONS

Non-Final Office Action dated Jun. 29, 2020 in U.S. Appl. No. 16/250,100.
Bhandari et al, Expression of Somatostatin and Somatostatin Receptor Subtypes 1-5 in Human Normal and Diseased Kidney, Journal of Histochemistry & Cytochemistry, 2008, 56, pp. 733-743.
Van Keimpema et al., Lanreotide Reduces the Volume of Polycystic Liver: A Randomized, Double-Blind, Placebo-Controlled Trial, Gastroenterology, 2009, 137, pp. 1661-1668.
Modlin et al, Review article: somatostatin analogues in the treatment of gastroenteropancreatic neuroendocrine (carcinoid) tumours, liment Pharmacol Ther, 2010, 31, pp. 169-188.
"The Comparison of Somatostatin and Octreotide", Happy little pharmacist, [Internet] <http://mulicia.pixnet.net/blog/post/21531460-somatostatin-%E8%88%87octreotide% . . . > pp. 1-9 retrieved on Oct. 13, 2016.
Communication dated Jan. 31, 2017 from the Japanese Patent Office in counterpart Japanese application No. 2014-555000.
Tallarida; "Drug Synergism and Dose-Effect Data Analysis" CRC Press LLC, pp. 1-29 (2000).
Hogan et al., "Randomized Clinical Trial of Long-Acting Somatostatin for Autosomal Dominant Polycystic Kidney and Liver Disease", Journal of the American Society of Nephrology, 21(6):1052-1061 (2010).
Gattone II et al., "Inhibition of renal cystic disease development and progression by a vasopressin V2 receptor antagonist", Nature Medicine, 9(10):1323-1326 (2003).
Wang, et al., "Effectiveness of Vasopressin V2 Receptor Antagonists OPC-31260 and OPC-41061 on Polycystic Kidney Disease Development in the PCK Rat", J Am Soc Nephrol., 16:846-851 (2005).
Polycystic Kidney Disease, retrieved from http://www.niddk.nih.gov/health-information/health-topics/kidneydisease/polycystic-kidneydisease-pkd/Pages/facts.aspx, pp. 1-16 (accessed Oct. 19, 2015).
International Search Report for PCT/JP2013/065637 dated Aug. 20, 2013.
Masyuk et al., "Pasireotide is More Effective than Octreotide in Reducing Hepatorenal Cystogenesis in Rodents with Polycystic Kidney and Liver Diseases", Hepatology, 58(1):409-421 (2013).
Patel et al., "Advances in the Pathogenesis and Treatment of Polycystic Kidney Disease", Current Opinion in Nephrology and Hypertension, 18(2):99-106 (2009).
Zmily et al., "Tolvaptan, hyponatremia, and heart failure", International Journal of Nephrology and Renovascular Disease, 4:57-71 (2011).
Chang et al., "Mechanism-Based Therapeutics for Autosomal Dominant Polycystic Kidney Disease: Recent Progress and Future Prospects", Nephron Clinical Practice, 120(1):c25-c35 (2012).
Gattone II et al., "Novel Therapies for Polycystic Kidney Disease", Genetic Syndromes & Gene Therapy, S4, pp. 1-9 (2011).
Torres, "Vasopressin antagonists in polycystic kidney disease", Seminars in Nephrology, 28:306-317 (2008).
Torres, "Role of Vasopressin Antagonists", Clinical Journal of the American Society of Nephrology, 3(4):1212-1218 (2008).
Communication dated Oct. 31, 2017 from the Japanese Patent Office in counterpart application No. 2017-024505.
Written Opinion for PCT/JP2013/065637 dated Aug. 20, 2015.
Hoag, The Impact of Formulation on Bioavailability: Summary of Workshop Discussion, J. Nutr., 2001, 131, pp. 1389S-1391S.

\* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Phe Trp Lys Thr
1

DRUG FOR PREVENTING AND/OR TREATING POLYCYSTIC KIDNEY DISEASE

CROSS-REFERENCE TO RELATED APPLICATIONS

This is a divisional of U.S. application Ser. No. 16/225,255 (now U.S. Pat. No. 11,147,821, issued Oct. 19, 2021), which is a continuation of U.S. application Ser. No. 15/473,032, filed Mar. 29, 2017 (now abandoned), which is a Divisional of U.S. application Ser. No. 14/402,540, filed Nov. 20, 2014 (now U.S. Pat. No. 9,636,382, issued May 2, 2017), which is a 371 National Stage Entry of International Application No. PCT/JP2013/065637, filed May 30, 2013; which claims priority from U.S. Provisional Application No. 61/653,524, filed May 31, 2012; the contents of all of which are incorporated herein by reference in their entirety.

TECHNICAL FIELD

The present invention relates to a drug for preventing and/or treating polycystic kidney disease (PKD).

BACKGROUND ART

Polycystic kidney disease is classified into ADPKD (autosomal dominant polycystic kidney disease) and ARPKD (autosomal recessive polycystic kidney disease). In both types of polycystic kidney disease, many cysts develop in the cortex and medulla of the kidney, leading to kidney dysfunction accompanied by substantial atrophy and fibrosis. As the disease progresses, the kidneys develop hypertrophy, leading to kidney failure requiring dialysis.

In cyst epithelial cells wherein cysts develop from tubular cells, cyclic AMP (cAMP) activates protein kinase A (PKA), and a series of MAP kinase (MAPK) pathways are activated to induce cell proliferation. In the cyst epithelial cells, the expression of vasopressin receptor (V2R) is enhanced and adenylate cyclase activity is elevated, which further increases cAMP levels and accelerates cell proliferation.

Vasopressin receptor antagonists have been reported to have complete response in animal models of polycystic kidney disease, and tolvaptan is advancing in clinical trials (see, for example, Patent Literature (PTL) 1 and Non-patent Literature (NPL) 1, 2, and 3).

Octreotide, which is a somatostatin derivative that suppresses adenylate cyclase activity, is also expected to be useful as an agent for treating ADPKD, and clinical test results therefor have recently been reported (see Non-patent Literature (NPL) 4).

CITATION LIST

Patent Literature

PTL 1: JP4-154765A

Non-Patent Literature

NPL 1: Nat. Med., 2003, 9(10):1323-6
NPL 2: J. Am. Soc. Nephrol., 2005, 16:846-851
NPL 3: Clin. J. Am. Soc. Nephrol. 2008, 3:1212-1218
NPL 4: J. Am. Soc. Nephrol., 2010, 21:1052-1061

SUMMARY OF INVENTION

Technical Problem

An object of the present invention is to provide a combination drug that has remarkably excellent preventive and/or therapeutic effects on polycystic kidney disease.

Solution to Problem

To solve the above problem, the present inventors conducted extensive research on combination drugs that can remarkably increase preventive and/or therapeutic effects on polycystic kidney disease. As a result, the inventors confirmed that the combined use of tolvaptan and a somatostatin derivative, octreotide, can produce remarkable therapeutic effects (e.g., reduction of kidney weight) on polycystic kidney disease, compared to the use of either compound alone. Further, the inventors confirmed that a combination of tolvaptan and the somatostatin derivative can provide remarkable therapeutic effects on polycystic kidney disease, even when the dose of the tolvaptan and/or the somatostatin derivative is so low as to be ineffective if either of the compounds is used alone. As a result of further research based on this finding, the present invention has been accomplished.

More specifically, the present invention provides the following combination drugs.

Item 1. A drug for preventing and/or treating polycystic kidney disease comprising a combination of tolvaptan or a prodrug thereof with a somatostatin derivative.

Item 2. The drug according to Item 1 comprising a combination of a pharmaceutical composition (a pharmaceutical preparation) comprising tolvaptan or a prodrug thereof with a pharmaceutical composition (a pharmaceutical preparation) comprising a somatostatin derivative.

Item 3. The drug according to Item 1 or 2 comprising a low dose of tolvaptan or a prodrug thereof that would be ineffective if used alone.

Item 4. The drug according to any one of Items 1 to 3 wherein the somatostatin derivative is octreotide, pasireotide, lanreotide, vapreotide, or a salt thereof.

Item 5. The drug according to any one of Items 1 to 4 which is a combination of an orally administered drug comprising tolvaptan or a prodrug thereof and an injectable preparation comprising a somatostatin derivative.

Item 6. The drug according to Item 5 wherein the injectable preparation comprising the somatostatin derivative is a subcutaneously administered drug.

Item 7. The drug according to Item 5 wherein the injectable preparation comprising the somatostatin derivative is an intramuscularly administered drug.

Item 8. Use of a combination of tolvaptan or a prodrug thereof with a somatostatin derivative in the manufacture of a drug for preventing and/or treating polycystic kidney disease.

Item 9. A drug comprising a combination of tolvaptan or a prodrug thereof with a somatostatin derivative for use in the prevention and/or treatment of polycystic kidney disease.

Item 10. A method for treating polycystic kidney disease, comprising administering tolvaptan or a prodrug thereof in combination with a somatostatin derivative to a polycystic kidney disease patient.

Item 11. The method according to Item 10 wherein the tolvaptan or prodrug thereof is orally administered and the somatostatin derivative is subcutaneously or intramuscularly administered to the polycystic kidney disease patient.

Item 12. A kit for preventing and/or treating polycystic kidney disease comprising an orally administered drug comprising tolvaptan or a prodrug thereof and an injectable preparation (in particular, a subcutaneously administered drug or an intramuscularly administered drug) comprising a somatostatin derivative.

Item 13. The drug according to any one of Items 1 to 7 wherein the tolvaptan or a prodrug thereof is tolvaptan and the somatostatin derivative is octreotide.

Item 14. The use according to Item 8 wherein the tolvaptan or a prodrug thereof is tolvaptan and the somatostatin derivative is octreotide.

Item 15. The drug according to Item 9 wherein the tolvaptan or a prodrug thereof is tolvaptan and the somatostatin derivative is octreotide.

Item 16. The method according to Item 10 or 11 wherein the tolvaptan or a prodrug thereof is tolvaptan and the somatostatin derivative is octreotide.

Item 17. The kit according to Item 12 wherein the tolvaptan or a prodrug thereof is tolvaptan and the somatostatin derivative is octreotide.

Advantageous Effects of Invention

The drug comprising a combination of tolvaptan or a prodrug thereof with a somatostatin derivative according to the present invention provides remarkable therapeutic effects on polycystic kidney disease (e.g., a kidney weight increase-suppressing effect, a renal function-improving effect, etc.), compared to either compound used alone. A combination of tolvaptan or a prodrug thereof with a somatostatin derivative provides remarkable therapeutic effects on polycystic kidney disease, even when the dose of tolvaptan or a prodrug thereof and/or the somatostatin derivative is so low as to be ineffective if either compound is used alone.

Because the combination drug of the present invention can thereby maintain drug efficacy while reducing side effects, the provision of high therapeutic effects while maintaining the quality of life (QOL) of polycystic kidney disease patients can be expected.

DESCRIPTION OF EMBODIMENTS

A feature of the drug for preventing and/or treating polycystic kidney disease according to the present invention is that it comprises a combination of tolvaptan or a prodrug thereof with a somatostatin derivative.

1. Tolvaptan and a Prodrug Thereof

Tolvaptan is the common name for 7-chloro-5-hydroxy-1-[2-methyl-4-(2-methylbenzoylamino)benzoyl]-2,3,4,5-tetrahydro-1H-benzoazepine, represented by Formula (1).

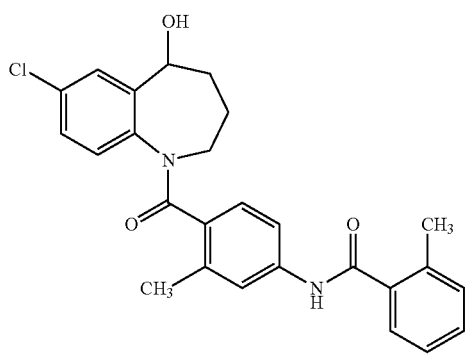

(1)

Tolvaptan contains a hydroxy-bonded carbon atom as an asymmetric carbon, as shown in Formula (I). Therefore, tolvaptan has a pair of enantiomers (R- and S-enantiomers) based on the asymmetric carbon. The term "tolvaptan" is used to include R enantiomer, S enantiomer, and a mixture of the two enantiomers in any proportion. Tolvaptan is preferably R enantiomer, S enantiomer, or a racemic compound (an equal mixture of R enantiomer and S enantiomer); and is more preferably a racemic compound.

Tolvaptan may be crystalline, amorphous, or a mixture of the two. When crystals have two or more polymorphisms, tolvaptan includes all of the polymorphisms.

Tolvaptan may be such that one or more atoms in the molecule of the tolvaptan are replaced by one or more isotopes thereof. Examples of such isotopes include deuterium ($^2$H), tritium ($^3$H), $^{13}$C, $^{14}$N, $^{18}$O, and the like.

Tolvaptan may be in the form of, for example, an anhydride, a solvate (e.g., a hydrate, an alcoholate, etc.), a salt, or co-crystals.

Tolvaptan may be a prodrug. The prodrug is a compound obtained by modifying an active compound (tolvaptan) in consideration of improved solubility in water, improved stabilization, improved bioavailability, etc.

An example of a prodrug is a compound produced by phosphorylation of the hydroxy group of tolvaptan. Specific examples thereof include a benzazepine compound represented by the following Formula (1a) or a salt thereof, which is disclosed in JP2009-521397A.

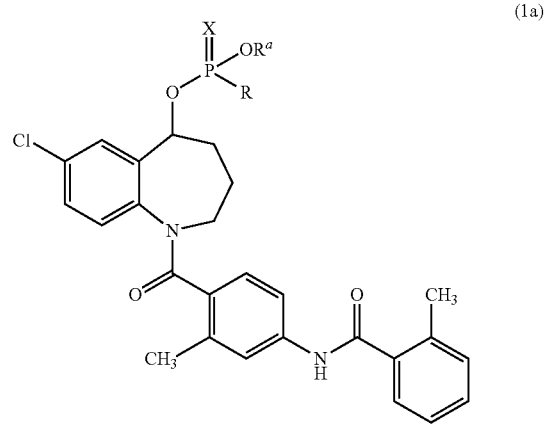

(1a)

(wherein R is a hydrogen atom, a hydroxy group optionally having a protecting group, a mercapto group optionally having a protecting group, or an amino group optionally having one or two protecting groups; $R^a$ is a hydrogen atom or a hydroxy-protecting group; and X is an oxygen atom or a sulfur atom).

In Formula (1a), there is no particular limitation on the "protecting group" for the hydroxy group optionally having a protecting group, the mercapto group optionally having a protecting group, or the amino group optionally having one or two protecting groups, represented by R. Typical examples of protecting groups include lower alkyl groups (for example, $C_{1-6}$ alkyl groups, such as methyl and ethyl), phenyl-lower alkyl groups (for example, phenyl-$C_{1-6}$ alkyl groups, such as benzyl and phenethyl), lower alkoxycarbonyl groups (for example, $C_{1-6}$ alkoxycarbonyl groups, such as methoxycarbonyl, ethoxycarbonyl, and tert-butoxycarbonyl), and the like.

Examples of the hydroxy protecting group represented by $R^a$ in Formula (1a) are those mentioned above as examples of the "protecting group" included in R.

Other examples of prodrugs include a compound obtained by acylating the hydroxy group of tolvaptan. Specific examples thereof include a benzazepine compound represented by the following formula (1b) or a salt thereof, which are disclosed in WO2009/001968 (JP2010-531293A).

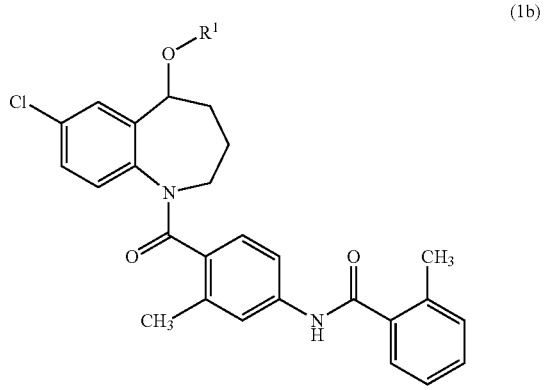

(1b)

wherein $R^1$ is a group of (1-1) to (1-7) below:
(1-1) a —CO—$(CH_2)_n$—$COR^2$ group
(wherein n is an integer of 1 to 4, $R^2$ is (2-1) a hydroxy group;
(2-2) a lower alkoxy group optionally substituted with a hydroxy group, a lower alkanoyl group, a lower alkanoyloxy group, a lower alkoxycarbonyloxy group, a cycloalkyloxycarbonyloxy group, or 5-methyl-2-oxo-1,3-dioxol-4-yl; or
(2-3) an amino group optionally substituted with a hydroxy-lower alkyl group);
(1-2) a —CO—$(CH_2)_m$—$NR^3R^4$ group
(wherein m is an integer of 0 to 4, $R^3$ is a hydrogen atom or a lower alkyl group, $R^4$ is (4-1) a hydrogen atom; (4-2) a lower alkyl group optionally substituted with a halogen atom, a lower alkylamino group, a lower alkoxycarbonyl group, or 5-methyl-2-oxo-1,3-dioxol-4-yl; or (4-3) a lower alkoxycarbonyl group optionally substituted with a halogen atom, a lower alkanoyloxy group, or 5-methyl-2-oxo-1,3-dioxol-4-yl, $R^3$ and $R^4$ may form a 5- or 6-membered saturated heterocyclic ring by bonding $R^3$ and $R^4$ to each other, together with the nitrogen atom to which $R^3$ and $R^4$ bond, directly or via a nitrogen atom or oxygen atom, the heterocyclic ring being optionally substituted with (4-4) a lower alkyl group (the lower alkyl group being optionally substituted with a hydroxy-lower alkoxy group); (4-5) a lower alkoxycarbonyl group; (4-6) an alkylcarbonyl group (the alkyl group being optionally substituted with a carboxyl group or a lower alkoxycarbonyl group); (4-7) an arylcarbonyl group; or (4-8) a furylcarbonyl group);
(1-3) a —CO—$(CH_2)_p$—O—CO—$NR^5R^6$ group
(wherein p is an integer of 1 to 4, $R^5$ is a lower alkyl group, and $R^6$ is a lower alkoxycarbonyl-lower alkyl group);
(1-4) a —CO—$(CH_2)_q$—X—$R^7$ group
(wherein q is an integer of 1 to 4, X is an oxygen atom, a sulfur atom, or a sulfonyl group, and $R^7$ is a carboxy-lower alkyl group, or a lower alkoxycarbonyl-lower alkyl group);
(1-5) a —CO—$R^8$ group
(wherein $R^8$ is (8-1) an alkyl group optionally substituted with a halogen atom, a lower alkanoyloxy group, or a phenyl group (the phenyl group being substituted with a dihydroxyphosphoryloxy group in which the hydroxy groups are optionally substituted with benzyl groups, and a lower alkyl group), (8-2) a lower alkoxy group substituted with a halogen atom, a lower alkanoyloxy group, or a dihydroxyphosphoryloxy group, (8-3) a pyridyl group, or (8-4) a lower alkoxyphenyl group);
(1-6) a lower alkyl group substituted with a group selected from the group consisting of lower alkylthio groups, a dihydroxyphosphoryloxy group, and lower alkanoyloxy groups; and
(1-7) an amino acid or peptide residue optionally protected with one or more protecting groups.

In Formula (1b), the term "lower" refers to "$C_{1-6}$", unless otherwise specified.

Examples of lower alkanoyl groups include straight or branched $C_{2-6}$ alkanoyl groups, such as acetyl, n-propionyl, n-butyryl, isobutyryl, n-pentanoyl, tert-butylcarbonyl, and n-hexanoyl.

Examples of lower alkanoyloxy groups include straight or branched $C_{2-6}$ alkanoyloxy groups, such as acetyloxy, n-propionyloxy, n-butyryloxy, isobutyryloxy, n-pentanoyloxy, tert-butylcarbonyloxy, and n-hexanoyloxy.

Examples of lower alkoxycarbonyloxy groups include alkoxycarbonyloxy groups in which the alkoxy moiety is a straight or branched $C_{1-6}$ alkoxy group, such as methoxycarbonyloxy, ethoxycarbonyloxy, n-propoxycarbonyloxy, isopropoxycarbonyloxy, n-butoxycarbonyloxy, isobutoxycarbonyloxy, tert-butoxycarbonyloxy, sec-butoxycarbonyloxy, n-pentyloxycarbonyloxy, neopentyloxycarbonyloxy, n-hexyloxycarbonyloxy, isohexyloxycarbonyloxy, and 3-methyl pentyloxycarbonyloxy.

Examples of cycloalkyloxycarbonyloxy groups include cycloalkyloxycarbonyloxy groups in which the cycloalkyl moiety is a $C_{3-8}$ cycloalkyl group, such as cyclopropyloxycarbonyloxy, cyclobutyloxycarbonyloxy, cyclopentyloxycarbonyloxy, cyclohexyloxycarbonyloxy, cycloheptyloxycarbonyloxy, and cyclooctyloxycarbonyloxy.

Examples of cycloalkylcarbonyl groups include cycloalkylcarbonyl groups in which the cycloalkyl moiety is a $C_{3-8}$ cycloalkyl group, such as cyclopropylcarbonyl, cyclobutylcarbonyl, cyclopentylcarbonyl, cyclohexylcarbonyl, cycloheptylcarbonyl, and cyclooctylcarbonyl.

Examples of lower alkoxy groups include straight or branched $C_{1-6}$ alkoxy groups, such as methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy, and 3-methylpentyloxy.

Examples of hydroxy-lower alkyl groups include straight or branched $C_{1-6}$ alkyl groups having one to three hydroxy groups, such as hydroxymethyl, 2-hydroxyethyl, 1-hydroxyethyl, 3-hydroxypropyl, 2,3-dihydroxypropyl, 4-hydroxybutyl, 3,4-dihydroxybutyl, 1,1-dimethyl-2-hydroxyethyl, 5-hydroxypentyl, 6-hydroxyhexyl, 3,3-dimethyl-3-hydroxypropyl, 2-methyl-3-hydroxypropyl, and 2,3,4-trihydroxybutyl.

Examples of alkyl groups include straight or branched $C_{1-10}$ alkyl groups such as methyl, ethyl, n-propyl, isopropyl, n-butyl, isobutyl, tert-butyl, sec-butyl, n-pentyl, isopentyl, neopentyl, n-hexyl, isohexyl, and 3-methylpentyl.

Examples of lower alkyl groups include straight or branched $C_{1-6}$ alkyl groups, such as methyl, ethyl, n-propyl, isopropyl, n-butyl, isobutyl, tert-butyl, sec-butyl, n-pentyl, isopentyl, neopentyl, n-hexyl, isohexyl, and 3-methylpentyl.

Examples of halogen atoms include fluorine, chlorine, bromine, and iodine.

Examples of lower alkylamino groups include amino groups substituted with one to two straight or branched $C_{1-6}$ alkyl groups, such as methylamino, ethylamino, n-propylamino, isopropylamino, n-butylamino, tert-butylamino, n-pentylamino, n-hexylamino, dimethylamino, diethylamino, di-n-propylamino, di-n-butylamino, di-n-pentylamino, di-n-hexylamino, N-methyl-N-ethylamino, N-ethyl-N-n-propylamino, N-methyl-N-n-butylamino, and N-methyl-N-n-hexylamino.

Examples of lower alkoxycarbonyl groups include alkoxycarbonyl groups in which the alkoxy moiety is a straight or branched $C_{1-6}$ alkoxy group, such as methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, n-pentyloxycarbonyl, neopentyloxycarbonyl, n-hexyloxycarbonyl, isohexyloxycarbonyl, and 3-methylpentyloxycarbonyl.

Examples of 5- or 6-membered saturated heterocyclic rings formed by bonding $R^3$ and $R^4$ to each other, together with the nitrogen atom to which $R^3$ and $R^4$ bond, directly or via a nitrogen atom or oxygen atom include pyrrolidine, imidazolidine, piperazine, piperidine, and morpholine.

Examples of hydroxy-lower alkoxy groups include hydroxyalkoxy groups that have one or two hydroxy groups, the alkoxy moiety being a straight or branched $C_{1-6}$ alkoxy group, such as hydroxymethoxy, 2-hydroxyethoxy, 1-hydroxyethoxy, 3-hydroxypropoxy, 4-hydroxybutoxy, 5-hydroxypentyloxy, 6-hydroxyhexyloxy, 1,1-dimethyl-2-hydroxyethoxy, and 2-methyl-3-hydroxypropoxy.

Examples of alkylcarbonyl groups include alkylcarbonyl groups in which the alkyl moiety is a straight or branched $C_{1-20}$ alkyl group, such as methylcarbonyl, ethylcarbonyl, n-propylcarbonyl, isopropylcarbonyl, n-butylcarbonyl, isobutylcarbonyl, tert-butylcarbonyl, sec-butylcarbonyl, n-pentylcarbonyl, isopentylcarbonyl, neopentylcarbonyl, n-hexylcarbonyl, isohexylcarbonyl, 3-methylpentylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, and n-icosylcarbonyl.

Examples of arylcarbonyl groups include phenylcarbonyl and (1- or 2-)naphthylcarbonyl.

Examples of furylcarbonyl groups include (2- or 3-)furylcarbonyl.

Examples of lower alkoxycarbonyl-lower alkyl groups include alkoxycarbonylalkyl groups in which the alkoxy moiety is a straight or branched $C_{1-6}$ alkoxy group, and the alkyl moiety is a straight or branched $C_{1-6}$ alkyl group, such as methoxycarbonylmethyl, ethoxycarbonylmethyl, 2-methoxycarbonylethyl, 2-ethoxycarbonylethyl, 1-ethoxycarbonylethyl, 3-methoxycarbonylpropyl, 3-ethoxycarbonylpropyl, 4-ethoxycarbonylbutyl, 5-isopropoxycarbonylpentyl, 6-n-propoxycarbonylhexyl, 1,1-dimethyl-2-n-butoxycarbonylethyl, 2-methyl-3-tert-butoxycarbonylpropyl, 2-n-pentyloxycarbonylethyl, and n-hexyloxycarbonylmethyl.

Examples of carboxy-lower alkyl groups include carboxyalkyl groups in which the alkyl moiety is a straight or branched $C_{1-6}$ alkyl group, such as carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, and 2-methyl-3-carboxypropyl.

Examples of lower alkoxyphenyl groups include alkoxyphenyl groups in which the alkoxy moiety is a straight or branched $C_{1-6}$ alkoxy group, such as methoxyphenyl, ethoxyphenyl, n-propoxyphenyl, isopropoxyphenyl, n-butoxyphenyl, isobutoxyphenyl, tert-butoxyphenyl, sec-butoxyphenyl, n-pentyloxyphenyl, isopentyloxyphenyl, neopentyloxyphenyl, n-hexyloxyphenyl, isohexyloxyphenyl, and 3-methylpentyloxyphenyl.

Examples of lower alkylthio groups include straight or branched $C_{1-6}$ alkylthio groups, such as methylthio, ethylthio, n-propylthio, isopropylthio, n-butylthio, tert-butylthio, n-pentylthio, and n-hexylthio.

Examples of amino acid or peptide residues include amino acid residues such as alanyl, phenylalanyl, sarcosyl, valyl, leucyl, isoleucyl, prolyl, N-ethylglycyl, N-propylglycyl, N-isopropylglycyl, N-butylglycyl, N-tert-butylglycyl, N-pentylglycyl, N-hexylglycyl, N,N-diethylglycyl, N,N-dipropylglycyl, N,N-dibutylglycyl, N,N-dipentylglycyl, N,N-dihexylglycyl, N-methyl-N-ethylglycyl, N-methyl-N-propylglycyl, N-methyl-N-butylglycyl, N-methyl-N-pentylglycyl, and N-methyl-N-hexylglycyl; and peptide residues such as sarcosyl-glycyl, glycyl-glycyl, glycyl-sarcosyl, sarcosyl-sarcosyl, alanyl-glycyl, phenylalanyl-glycyl, phenylalanyl-phenylalanyl, glycyl-glycyl-glycyl, N-ethylglycyl-glycyl, N-propylglycyl-glycyl, N,N-dimethylglycyl-glycyl, N,N-diethylglycyl-glycyl, N-methyl-N-ethylglycyl-glycyl, sarcosyl-glycyl-glycyl, N-ethylglycyl-glycyl-glycyl, and N,N-dimethylglycyl-glycyl-glycyl.

Examples of protecting groups for amino acids or peptides include those usually used to protect amino groups of amino acids or peptides, such as tert-butoxycarbonyl, benzyloxycarbonyl, fluorenylmethoxycarbonyl, and acetyl.

In this specification, a prodrug of tolvaptan (in particular, a compound of Formula (1a) and/or a compound of Formula (1b)) can be used together with or substituted for tolvaptan. In the present invention, tolvaptan is preferable.

2. Somatostatin Derivative

The term "somatostatin derivative" refers to somatostatin, a compound comprising an amino acid sequence (Phe-Trp-Lys-Thr) (SEQ ID NO: 1) essential for the physiological activity of somatostatin; or salts thereof. Specific examples thereof include somatostatin, octreotide, pasireotide, lanreotide, vapreotide, and the like. Such compounds can be used singly, or in a combination of two or more. Octreotide is preferable.

Octreotide refers to a cyclic polypeptide represented by Formula (2), and is the common name for (−)-D-phenylalanyl-L-cysteinyl-L-phenylalanyl-D-tryptophyl-L-lysyl-L-threonyl-N-[(1R,2R)-2-hydroxy-1-(hydroxymethyl)propyl]-L-cysteinamide cyclic (2→7) disulfide.

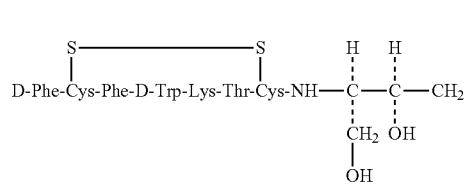

(2)

The somatostatin derivative may form a salt with a pharmaceutically acceptable acid. Examples of such acids include inorganic acids such as hydrochloric acid, hydrobromic acid, nitric acid, sulfuric acid, and phosphoric acid; and organic acids such as methanesulfonic acid, p-toluenesulfonic acid, acetic acid, citric acid, tartaric acid, maleic acid, fumaric acid, malic acid, and lactic acid. The salt of the somatostatin derivative is preferably hydrochloride or acetate, and more preferably diacetate of octreotide. This is commercially available under the trade name "SANDOSTATIN®" (a product of Novartis Pharma K.K.).

3. Pharmaceutical Preparation

A feature of the drug for preventing and/or treating polycystic kidney disease according to the present invention is that it comprises a combination of tolvaptan or a prodrug thereof with a somatostatin derivative. The combination is preferably a combination of tolvaptan with a somatostatin derivative. A combination of tolvaptan with octreotide, a combination of tolvaptan with pasireotide, a combination of tolvaptan with lanreotide, or a combination of tolvaptan with vapreotide is more preferable. A combination of tolvaptan with octreotide is even more preferable. These combinations apply to the entire invention.

The drug of the present invention may be in the foam of a single formulation (a mixture) comprising tolvaptan or a prodrug thereof with a somatostatin derivative; or in the form of separate formulations (concomitants), one of the formulations comprising tolvaptan or a salt thereof, and the other comprising a somatostatin derivative. The drug is preferably concomitants.

One example of such concomitants is a combination of a pharmaceutical composition (a pharmaceutical preparation) comprising tolvaptan or a prodrug thereof with a pharmaceutical composition (a pharmaceutical preparation) comprising a somatostatin derivative.

The pharmaceutical preparation comprising a combination of tolvaptan or a prodrug thereof with a somatostatin derivative may be a mixture or concomitants, and the dosage form of the pharmaceutical preparation can be suitably selected from those described below.

The pharmaceutical preparation can be produced by incorporating tolvaptan or a prodrug thereof and/or a somatostatin derivative by a conventional method using a commonly used diluent and/or excipient, such as a filler, an extender, a binder, a humectant, a disintegrator, a surfactant, and a lubricant.

The form of the pharmaceutical preparation can be suitably selected from various forms according to the therapeutic purpose. Typical examples of such forms include tablets, pills, powders, liquids, suspensions, emulsions, granules, capsules, suppositories, ointments, injections (solutions, suspensions, emulsions, etc.), and the like.

To form tablets, various carriers known in the art can be used. Examples of such carriers include excipients such as lactose, sucrose, sodium chloride, glucose, urea, starch, calcium carbonate, kaolin, and crystalline cellulose; binders such as water, ethanol, propanol, simple syrup, glucose solution, starch solution, gelatin solution, carboxymethyl cellulose, shellac, methylcellulose, potassium phosphate, and polyvinylpyrrolidone; disintegrators such as dry starch, sodium alginate, agar powder, laminaran powder, sodium hydrogen carbonate, calcium carbonate, polyoxyethylene sorbitan fatty acid esters, sodium lauryl sulfate, stearic acid monoglyceride, starch, and lactose; disintegration inhibitors such as sucrose, stearin, cacao butter, and hydrogenated oil; absorption promoters such as quaternary ammonium salts and sodium lauryl sulfate; humectants such as glycerol and starch; adsorbents such as starch, lactose, kaolin, bentonite, and colloidal silica; and lubricants such as purified talc, stearic acid salts, boric acid powder, and polyethylene glycol.

The tablets, if desired, can be coated with a general coating material to give coated tablets. Examples of such coated tablets include sugar-coated tablets, gelatin-coated tablets, enteric coated tablets, film-coated tablets, bilayer tablets, and multilayer tablets.

To form pills, various carriers known in the art can be used. Examples of such carriers include excipients such as glucose, lactose, starch, cacao butter, hydrogenated vegetable oil, kaolin, and talc; binders such as gum arabic powder, tragacanth powder, gelatin, and ethanol; and disintegrants such as laminaran and agar.

To form suppositories, various carriers known in the art can be used. Examples of such carriers include polyethylene glycol, cacao butter, higher alcohols, higher alcohol esters, gelatin, and semisynthetic glycerides.

Injections are preferably prepared in the form of solutions, emulsions, or suspensions that are sterilized and isotonic with blood. To form such solutions, emulsions, and suspensions using tolvaptan or a prodrug thereof and/or a somatostatin derivative, any diluents commonly used in the art can be used. Examples of such diluents include water, lactic acid aqueous solution, ethanol, propylene glycol, ethoxylated isostearyl alcohol, polyoxylated isostearyl alcohol, and polyoxyethylene sorbitan fatty acid ester. In this case, an isotonizing agent, such as sodium chloride, glucose, mannitol, or glycerol, may be incorporated into such a pharmaceutical preparation in an amount sufficient for making the preparation isotonic. Further, commonly used pH adjusters, solubilizers, buffers, soothing agents, etc., as well as coloring agents, preservatives, flavors, sweetening agents, and/or other medicines may be added, if necessary.

The amount of tolvaptan or a prodrug thereof and/or somatostatin derivative in the pharmaceutical preparation of the invention is not particularly limited insofar as it is a therapeutically effective amount as a combination drug, and can be suitably selected from a wide range. It is generally preferable that tolvaptan or a prodrug thereof and/or a somatostatin derivative are contained in the pharmaceutical preparation in a proportion of about 0.01 to about 70 wt %. For example, when concomitants are used as the combination drug, the pharmaceutical preparation comprising tolvaptan or a prodrug thereof typically comprises the tolvaptan or the prodrug thereof in an amount of 0.01 to 70 wt. %, and the pharmaceutical preparation comprising a somatostatin derivative typically comprises the somatostatin derivative in an amount of 0.01 to 70 wt. %.

4. Administration Method and Dosage

The method of administration (administration route) of the pharmaceutical preparation of the invention is not particularly limited. This preparation can be administered by a method suitable for the dosage form, the patient's age and sex, the status of the disease, and other conditions. For example, tablets, pills, liquids, suspensions, emulsions, granules, and capsules are administered orally. Injections are intravenously administered singly or as a mixture with a general injection transfusion, such as glucose solution or amino acid solution, or singly administered intramuscularly, intracutaneously, subcutaneously or intraperitoneally, as required. The suppositories are administered intrarectally.

Typical examples of the combination drug of the present invention are concomitants. One example of such concomitants is a combination of a pharmaceutical composition (a pharmaceutical preparation) comprising tolvaptan or a prodrug thereof with a pharmaceutical composition (a pharmaceutical preparation) comprising a somatostatin derivative. In this case, the pharmaceutical preparation comprising tolvaptan or a prodrug thereof may be, for example, an orally administered drug (an oral preparation), an intramuscularly administered drug (a sustained-release preparation), or an intravenously administered drug (a sustained-release preparation); the pharmaceutical preparation is preferably an oral preparation. The pharmaceutical preparation comprising a somatostatin derivative may be, for example, a subcutaneously administered drug (a subcutaneous injection), an intramuscularly administered drug (a sustained-release preparation), or an orally administered drug (an oral preparation), and is preferably a subcutaneously administered drug.

Examples of the combination of concomitants include, but are not limited to, a combination of an orally administered drug comprising tolvaptan or a prodrug thereof and a subcutaneously administered drug comprising a somatostatin derivative, and a combination of one drug comprising tolvaptan or a prodrug thereof and another drug comprising a somatostatin derivative, both being subcutaneously administered drugs (subcutaneous injections).

The dose of the combination drug of the present invention is suitably selected according to the dosage regimen, the patient's age and sex, the severity of the disease, and other conditions.

The dosage regimen of the pharmaceutical preparation comprising tolvaptan or a prodrug thereof is usually such that tolvaptan or a prodrug thereof is administered in an amount of about 0.001 to 300 mg, preferably 0.001 to 100 mg, per kg (body weight) per day in one or more administrations.

Even when tolvaptan or a prodrug thereof is administered in a low dose that would be ineffective if used alone, a combination thereof with a somatostatin derivative can provide excellent therapeutic effects on polycystic kidney disease. The dosage regimen of the pharmaceutical preparation comprising tolvaptan or a prodrug thereof when used in combination with a somatostatin derivative is such that tolvaptan or a prodrug thereof is administered in an amount of about 0.001 to 50 mg, and preferably 0.001 to 30 mg, per kg (body weight) per day in one or more administrations.

The dosage regimen of the preparation comprising a somatostatin derivative is usually such that the somatostatin derivative is administered in an amount of about 0.001 to 10 mg, preferably 0.001 to 1 mg, per kg (body weight) per day in one or more administrations.

The pharmaceutical preparation comprising tolvaptan or a prodrug thereof with the pharmaceutical preparation comprising a somatostatin derivative can be administered to a human (in particular, a patient) simultaneously or with a delay between administrations.

The present invention includes use of a combination of tolvaptan or a prodrug thereof with a somatostatin derivative in the manufacture of a drug for preventing and/or treating polycystic kidney disease.

The present invention includes a combination drug of tolvaptan or a prodrug thereof and a somatostatin derivative for use in the prevention and/or treatment of polycystic kidney disease.

The present invention includes a method for treating polycystic kidney disease, comprising administering a combination of tolvaptan or a prodrug thereof with a somatostatin derivative to a polycystic kidney disease patient. Preferable dosage forms are such that tolvaptan is administered orally and a somatostatin derivative is administered subcutaneously or intramuscularly.

The present invention includes a kit for preventing and/or treating polycystic kidney disease comprising an orally administered drug comprising tolvaptan or a prodrug thereof and an injectable preparation (in particular, a subcutaneously administered drug or an intramuscularly administered drug) comprising a somatostatin derivative. Examples of the kit include a kit comprising a container containing an orally administered drug comprising tolvaptan or a prodrug thereof and a container containing a subcutaneously administered drug or an intramuscularly administered drug comprising a somatostatin derivative.

The entire contents and disclosures of each patent and reference disclosed herein are incorporated by reference.

EXAMPLES

The present invention will now be illustrated with the following examples. However, the invention is not limited thereto or thereby.

Example 1

Individual or combined effects of tolvaptan, which is a vasopressin receptor antagonist, and octreotide, which is a somatostatin analogue, against polycystic kidney disease were evaluated using pcy mice, which are PKD model animals.

The aforementioned pcy mice are adult polycystic kidney disease model mice, and the mode of inheritance is autosomal recessive. In DBA/2FG-pcy mice generated by introducing the pcy gene into DBA/2 mice, cysts were observed with the naked eye from the fourth week, and the kidney volume increased over time until the 30th week. It has been reported that compared to wild-type mice, pcy mice have increased renal cAMP levels and elevated renal mRNA levels of aquaporin-2 and vasopressin V2 receptor (V2R). For details, see Non-patent Literature (NPL) 1.

Based on the body weight at 4 weeks of age and the renal volume measured by MRI, the pcy mice (male) were divided into the following four groups (each group: 9 mice):
  (1) a control group;
  (2) a group receiving a feed containing 0.03% tolvaptan;
  (3) a group receiving octreotide (300 µg/kg×2/day sc); and
  (4) a group receiving a feed containing 0.03% tolvaptan, and octreotide (300 µg/kg×2/day sc).

As normal control mice, DBA/2JJcl mice (5 mice) were used. A 0.03% tolvaptan-containing MF feed was given to the groups receiving tolvaptan. A MF feed not containing tolvaptan was given to the other groups, i.e., the control group and the group receiving octreotide alone. SANDOSTATIN® subcutaneous injection (100 µg/ml) was diluted with physiological saline and subcutaneously injected in an amount of 300 µg/kg/10 ml to the group receiving octreotide twice a day, morning and evening.

The drug treatment was started from 5 weeks of age, and continued until 15 weeks of age. Urine was collected from each mouse at 14 weeks of age using metabolic cages for 19 hours, and urine volume and urinary albumin excretion were measured.

The DBA control mice and pcy mice were sacrificed under isoflurane anesthesia at 15 weeks of age to collect their blood, and right and left kidneys. Plasma parameters were measured from the obtained blood, and the weight of right and left kidneys was measured.

Table 1 shows the weight of the kidneys (% body weight) during autopsy. At 15 weeks of age, marked renal hypertrophy and cysts were observed in pcy control mice, compared to normal DBA mice. The kidney weight was increased 5.2-fold. Compared to the pcy control group, the group receiving 0.03% tolvaptan-containing feed and the group subcutaneously receiving octreotide did not exhibit significant kidney weight suppressive effects when either tolvaptan or octreotide was administered alone. In contrast, a significant kidney weight suppressive effect was observed in the group receiving both tolvaptan and octreotide ($p<0.01$), compared to the pcy control. The group receiving both tolvaptan and octreotide exhibited a significantly high kidney weight suppressive effect ($p<0.05$), compared to the groups receiving either tolvaptan or octreotide alone.

TABLE 1

Kidney weight of (15-week-old) pcy mice (body weight adjustment: %)

| | Group of mice | Number of mice | Kidney weight (% body weight) Mean ± SE | Assay results | |
|---|---|---|---|---|---|
| | | | | Comparison with the control group | Comparison with the group receiving both of tolvaptan and octreotide |
| 1 | Normal DBA | 5 | 1.53 ± 0.04 | — | — |
| 2 | Pcy control | 9 | 8.02 ± 0.66 | — | — |
| 3 | Pcy receiving 0.03% tolvaptan-containing feed alone | 9 | 7.28 ± 0.84 | NS | p < 0.05 |
| 4 | Pcy receiving octreotide alone (300 μg/kg × 2/day sc) | 9 | 6.68 ± 0.65 | NS | p < 0.05 |
| 5 | Pcy receiving both 0.03% tolvaptan-containing feed and octreotide (300 μg/kg × 2/day sc) | 9 | 4.87 ± 0.36 | p < 0.01 | — |

Each value indicates the average value ± SEM.
For comparison with the control group, Dunnett's test (both sides) was used.
For comparison of the group receiving both of tolvaptan and octreotide with the groups receiving either one of tolvaptan and octreotide, the closed testing procedure was used.
"NS" indicates non-significant.

The above results show that a combination of tolvaptan with octreotide can synergistically suppress cystic kidney enlargement and improve kidney functions.

The invention claimed is:

1. A combination for suppressing progression of polycystic kidney disease and/or treating polycystic kidney disease, wherein said combination comprises a synergistically effective amount of a sustained-release formulation of tolvaptan or a prodrug thereof, and a sustained-release formulation of vapreotide or a salt thereof.

2. The combination according to claim 1, wherein the combination is in the form of separate formulations, and is a combination of an oral preparation comprising the sustained-release formulation of tolvaptan or a prodrug thereof, and an injectable preparation comprising the sustained-release formulation of vapreotide or a salt thereof.

3. A kit for suppressing disease progression of polycystic kidney disease and/or treating polycystic kidney disease, wherein said kit comprises a synergistically effective amount of an oral sustained-release formulation of tolvaptan or a prodrug thereof, and an injectable sustained-release formulation of vapreotide or a salt thereof.

* * * * *